United States Patent [19]
Evans

[11] Patent Number: 5,239,993
[45] Date of Patent: Aug. 31, 1993

[54] DOSAGE INHALATOR PROVIDING OPTIMIZED COMPOUND INHALATION TRAJECTORY

[75] Inventor: Rix E. Evans, Wendell, N.C.

[73] Assignee: Glaxo Inc., Research Triangle Park, N.C.

[21] Appl. No.: 935,585

[22] Filed: Aug. 26, 1992

[51] Int. Cl.⁵ ............................................. A61M 15/00
[52] U.S. Cl. .............................. 128/203.15; 128/203.23; 128/203.24
[58] Field of Search ............... 128/203.15, 203.23, 128/203.21, 203.12, 203.24, 200.21, 200.24

[56] References Cited

U.S. PATENT DOCUMENTS

| | | | |
|---|---|---|---|
| 263,451 | 8/1882 | Adams | 128/203.15 |
| 2,573,918 | 11/1951 | McCuiston | 128/203.15 X |
| 2,587,215 | 2/1952 | Priestly | 128/203.15 |
| 2,633,131 | 3/1953 | Grosvenor | 128/203.23 |
| 4,240,418 | 12/1980 | Rosskamp et al. | 128/203.15 |
| 4,452,239 | 6/1984 | Malem | 128/200.17 |
| 5,161,524 | 11/1992 | Evans | 128/203.15 |

FOREIGN PATENT DOCUMENTS

| | | | |
|---|---|---|---|
| 0488609 | 6/1992 | European Pat. Off. | |
| 848035 | 7/1981 | U.S.S.R. | 128/203.15 |
| 9112040 | 8/1991 | World Int. Prop. O. | 128/203.14 |
| 9210229 | 6/1992 | World Int. Prop. O. | 128/200.14 |

OTHER PUBLICATIONS

"The Fluid Mechanics of Cromolyn Sodium Inhalers Used for Asthma Prevention" Eugene Niemi, Jr, Proceedings of 7th New England Bioengineering Conference, Troy, NY, 22-23 Mar. 1979.

Primary Examiner—Edgar S. Burr
Assistant Examiner—Eric Raciti
Attorney, Agent, or Firm—Richard E. Jenkins

[57] ABSTRACT

A breath actuated dry powder medicament inhalator has a primary air passageway therethrough defining a venturi in the medial portion thereof. A secondary air passageway is provided which includes a compound deaggregating swirl chamber and is fluidly connected to the venturi of the primary air passageway. A dry powder compound storage chamber and cooperatively associated metering plate act to introduce a predetermined amount of compound into the swirl chamber upon actuation of the metering plate. The primary air passageway is configured within the inhalator apparatus so as to create an optimized air flow trajectory through the mouth of the user to minimize dry powder compound impingement upon the outside radius of the throat.

14 Claims, 4 Drawing Sheets

DOSAGE INHALATOR PROVIDING OPTIMIZED COMPOUND INHALATION TRAJECTORY

TECHNICAL FIELD

The present invention relates to an inhalator apparatus for the inhalation of a medicament in dry powder form.

RELATED ART

The administration of powder form or pulverulent medicinal agents by inhalation for the treatment of diseases of the respiratory tract such as bronchial asthma and the like is well known. However, the search continues for a new and improved inhalator apparatus for administering predetermined doses of a medicament in powder form to address the aforementioned diseases of the respiratory tract.

Applicant is aware of two general classes of inhalation devices currently being commercially distributed for bronchial administration of selected doses of dry powder medicament. The first type of inhalation device known to applicant is a pressurized aerosol inhaler which serves to discharge a metered dose of the powder medicament suspended in a pharmaceutically inert liquid propellant. Although this type of inhalation device does consistently deliver a predetermined dose of medication, at least a portion of the medication is disadvantageously deposited on the back of the mouth and throat of the patient due to the high velocity at which the medicant is propelled.

A second type of commercial inhalation device known to applicant utilizes the patient's inhaled breath as a means to transport the dry powder medicant. These devices also suffer disadvantages well known in the art including a lack of air flow velocity regulating means which can result in excessive inhalation velocity during use so as to cause the powder medicament being inhaled to impinge upon the back of the mouth and throat. This prevents the totality of the powder medicament from successfully entering the desired destination site (the lungs of the patient). Other shortcomings and disadvantages of this type of inhalation device are also well known to those skilled in the art.

An effort to solve some of the problems associated with prior art inhalation devices is disclosed in U.S. Pat. No. 4,240,418 to Rosskamp et al. This apparatus utilizes the patient's inhaled breath as a vehicle to transport a powder medicament and is constructed from only a limited number of moving parts. A venturi is defined within the housing between the air inlet and air outlet. Gravity is relied on to deliver a medicinal agent from the storage area to a delivery area in the venturi of the apparatus from which it is dispensed through a mouthpiece or upturned nasal applicator tube.

Another inhalator apparatus of note is disclosed in applicant's own commonly assigned U.S. patent application Ser. No. 739,905 filed on Aug. 2, 1991, and now pending. This inhalator is a significant advancement in the second class of inhalators since it provides for a metered dosage inhalator with an automatic regulating means to provide a substantially constant predetermined maximum air flow velocity therethrough in order to minimize impingement of the powder medicament at the back of the upper throat. The apparatus disclosed and claimed in the aforementioned pending application is a very advantageous advancement in the art but utilizes a relatively complex automatic diaphragm mechanism to regulate air flow velocity. By contrast, the inhalator apparatus of the present invention addresses the same well-known prior art problem of impingement of powder compound upon the upper throat with an elegantly simple inhalator apparatus which will be described in specific detail hereinbelow.

DISCLOSURE OF THE INVENTION

Therefore, in accordance with the present invention, applicant provides a dosage inhalator apparatus for the inhalation of a predetermined amount of a pharmacologically active dry powder compound as an aerosol effluent which is designed specifically to overcome the inherent tendency of previous apparatus to dispense the drug in a straight trajectory which results in the undesirable deposition of the powder compound along the outside radius of the user's throat. The inhalator apparatus comprises an elongate housing defining a primary air passageway therethrough having a generally inclined air inlet portion at one end adapted to introduce air flow at an angle between about 5°-45° below a horizontal baseline, and an air exit portion at the other end for insertion into the mouth. The primary air passageway further includes a venturi portion substantially in the medial area thereof between the air inlet portion and the air exit portion.

A storage chamber is formed in the inhalator apparatus housing for storing the compound to be inhaled. A secondary air passageway is also provided in the inhalator apparatus housing having an air introduction portion at one end thereof adjacent the air inlet portion of the primary air passageway, and the other end thereof is positioned to fluidly communicate with the venturi portion of the primary air passageway. An enlarged compound swirl chamber is provided in the secondary air passageway between the air introduction portion and the other end thereof. Finally, a dose introduction means is provided within the housing for transporting a predetermined portion of the powder compound from the storage chamber to the compound swirl chamber of the secondary air passageway.

Thus, during inhalation the pressure differential between the venturi portion of the primary air passageway and the swirl chamber of the secondary air passageway serves to swirl the dry powder compound out of the swirl chamber and into the primary air passageway. The novel air flow pathway through the inhalator apparatus then serves to introduce the powder compound along an optimized arcuate trajectory to the pharynx and larynx of the user.

It is therefore the object of the present invention to provide an improved multi-dose dry powder inhalator apparatus.

It is another object of the present invention to provide an improved multi-dose dry powder inhalator apparatus which obviates dry powder inhalation problems due to excessive air flow velocity and/or incorrect air flow trajectory during inhalation.

It is yet another object of the present invention to provide an improved multi-dose dry powder inhalator apparatus which includes a swirl chamber to promote deaggregation of the dry powder metered dosage and which promotes an optimized air flow trajectory to the pharynx and larynx of the user to minimize undesirable powder compound deposition along the outside radius of the throat of the user.

Some of the objects of the invention having been stated, other objects will become evident as the description proceeds, when taken in connection with the accompanying drawings.

BEST MODE FOR CARRYING OUT THE INVENTION

As used in a specification of the present application, the term "dry powder medicament" means a dry powder substance used to achieve a therapeutic effect in respiratory therapy. The term "multi-dose dry powder inhalator" used herein means an apparatus that is capable of delivering more than one dose of dry powder medicament without refilling. The term "inhalation profile" used herein means the volume of air inhaled or exhaled as a function of time.

To fully appreciate the present invention, it should also be understood that air flow rate during inhalation while experiencing an asthma attack or other type of respiratory disease symptom is never steady, and complicating the situation is that the acceleration of air flow rate is seldom constant. A patient's duration of inhalation may be long or short, depending on each specific case and the age of the patient. Since an attack is generally an anxious moment for the patient, it is advantageous to have a dry powder compound medicament delivery apparatus that will automatically compensate for all of the aforementioned conditions and which possesses a dosage metering mechanism that requires no significant training to operate. Applicant's inhalator apparatus as described in detail hereinafter has been developed to meet this need.

Figure 1:
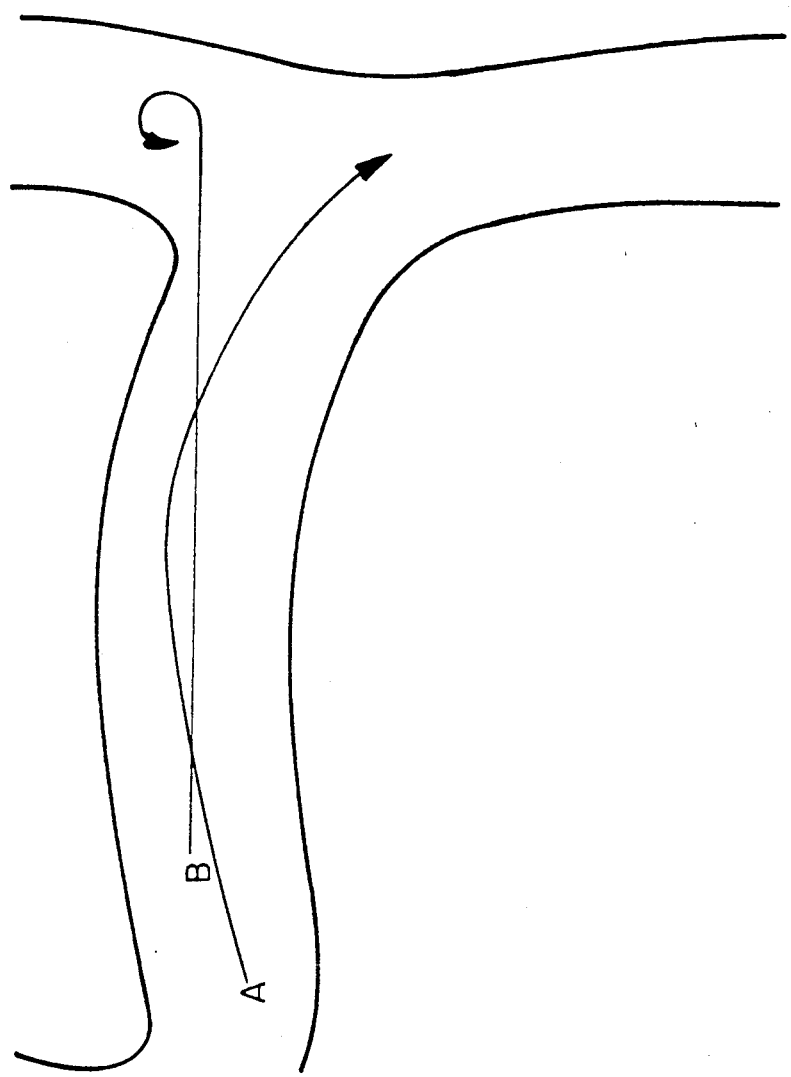
FIG. 1 is a schematic view of the mouth and throat of a human.

Referring now to the drawings, FIG. 1 illustrates a general profile of the mouth and pharynx of a human. All dry powder inhalators known to applicant discharge at approximately a right angle to the pharynx (see trajectory B) which maximizes two unfavorable conditions. The abrupt change of air flow direction necessitates a relatively significant force to overcome the inertia of the powder medicament particles which encourages deposition thereof onto the outside radius of the throat. Also, a phenomenon has been observed indicating vortex shedding of the dry powder medicament off the rear of the mouth roof which tends to induce unfavorable angular acceleration of the powder medicament and deposition thereof along the outside radius of the throat.

Figure 2:
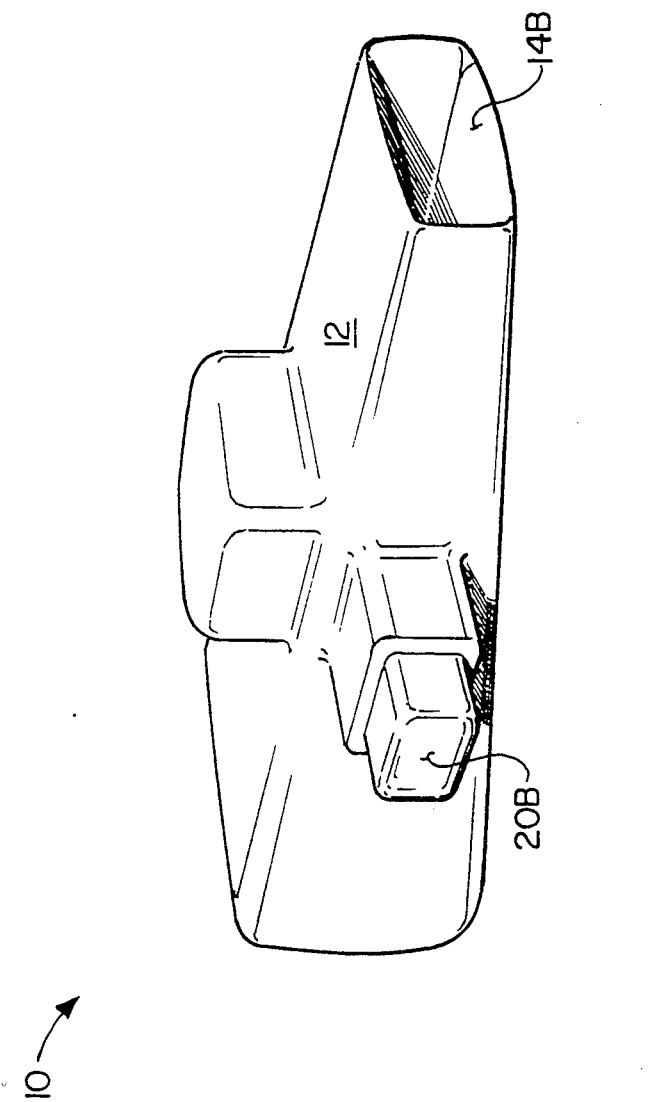
FIG. 2 is a perspective view of the dosage inhalator of the present invention.
Figure 3:
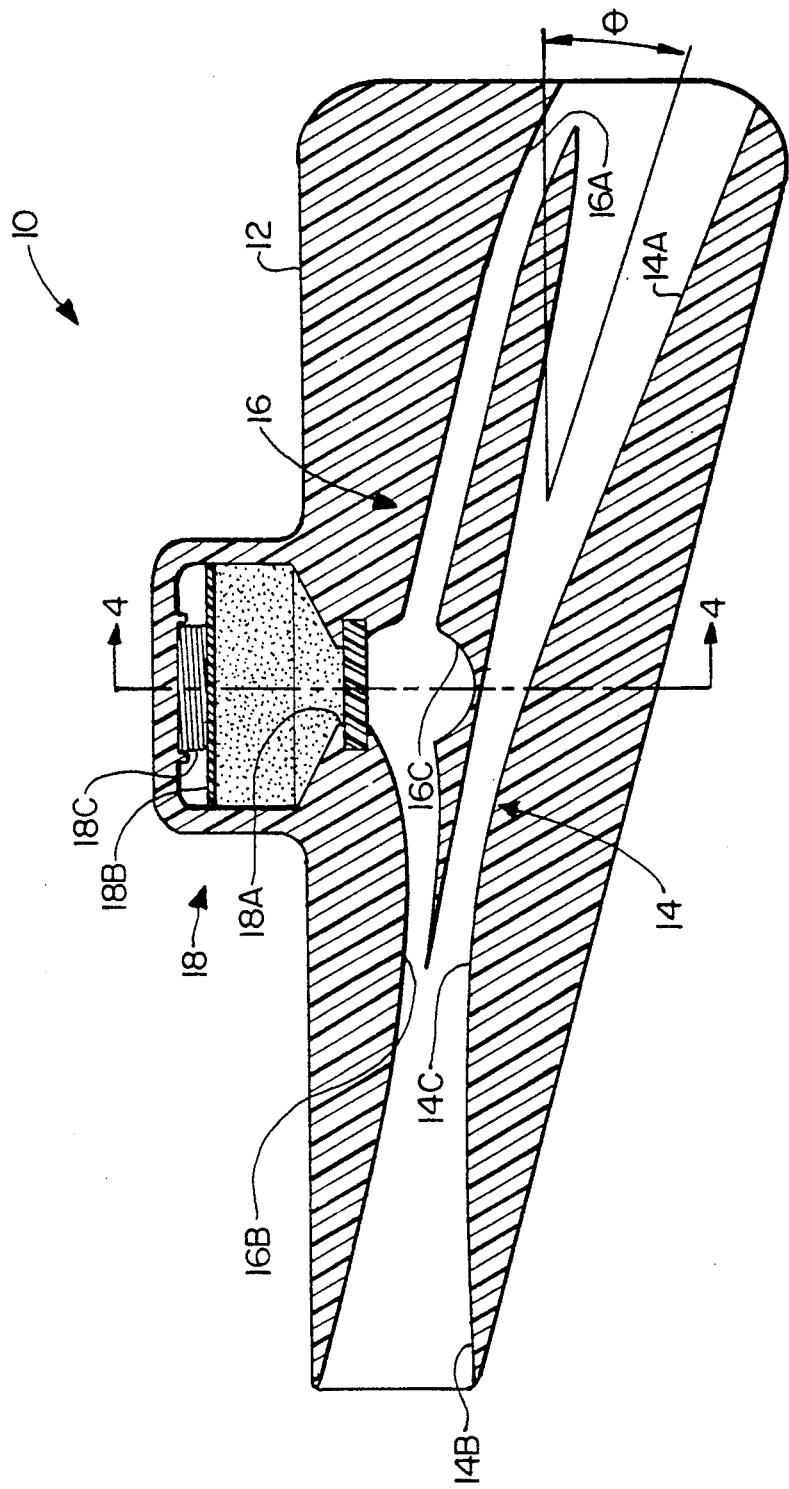
FIG. 3 is a vertical cross-sectional view of the dosage inhalator of FIG. 2.
Figure 4:
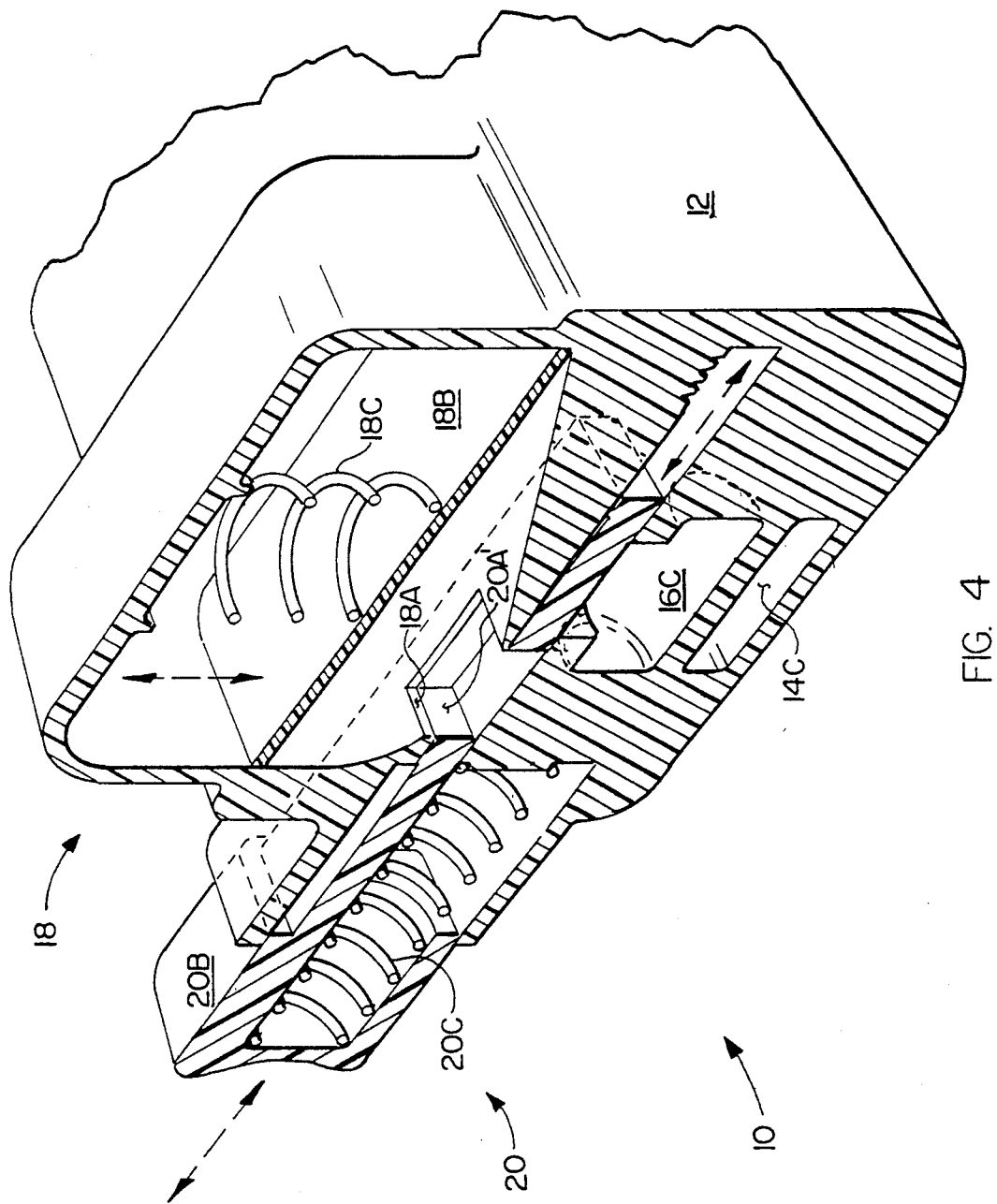
FIG. 4 is a horizontal cross-sectional view of the inhalator of FIG. 2 taken on line 4—4 of FIG. 3.

By contrast, applicant's novel inhalator apparatus 10 shown in FIGS. 2-4 serves to provide an arcuate air flow pathway through the mouth of a user (see trajectory A) which allows the compound medicament particles and air to better avoid deposition along the outside radius of the throat prior to introduction into the lungs. It has been found that the novel angular acceleration of the dry compound medicament particles more closely approximates a constant value which makes their destination much more consistent and tends to obviate vortex shedding and to thereby minimize the aforementioned associated dry powder medicament deposition at the back of the throat of the user.

Referring now specifically to FIGS. 2-4, inhalator apparatus 10 comprises a housing 12 which is preferably formed from a plastic material, although the housing may be made of any suitable material and is not intended to be limited to plastic. Housing 12 includes a primary air passageway 14 therethrough having an inlet end 14A, an outlet end 14B, and a venturi portion 14C formed in the medial area therebetween. The shape of primary air passageway 14 is critical to the functionality of inhalator apparatus 10. Referencing particularly FIG. 3, it can be seen that inlet end 14A provides an upwardly inclined trajectory through inhalator apparatus 10 which is between about 5 to 45 degrees below a horizontal reference line. Most suitably, the preferred air flow trajectory through inlet end 14A is at an angle $\theta$ of about 15 degrees below a horizontal reference line. This air flow trajectory through inlet end 14A of primary air passageway 14 serves to provide an optimized arcuate trajectory A (see FIG. 1) through the mouth and pharynx when the patient inhales by inserting outlet end 14B of inhalator apparatus 10 into his mouth.

A secondary air passageway 16 is provided in housing 12 and includes an air introduction portion 16A at one end adjacent inlet end 14A of primary air passageway 14. The other end 16B of air passageway 16 terminates in fluid communication with the aforementioned venturi portion 14C formed in primary passageway 14. Also, and very importantly to the efficacy of the present inventive inhalator apparatus 10, secondary air passage 16 defines an enlarged compound swirl chamber 16C between air introduction portion 16A and remote end 16B thereof. Dry powder medicament swirl chamber 16C serves to stage the metered powder dose since the chamber is not directly exposed to the main air flow of primary air passageway 14, and this serves to minimize the effect of any moisture from external air. Furthermore, the swirling action of the air flow created in the enlarged cylindrical chamber serves to promote deaggregation of the dry powder medicament particles from attendant excipients. Venturi 14C serves to sense the correct air flow profile envelope and, at that point, the dry powder medicament is pulled into the main air flow of primary air passageway 14 so as to be discharged by inhalator apparatus 10 along the optimized trajectory B (see FIG. 1) to the pharynx and larynx of the user.

Storage chamber 18 is also provided in housing 12 for storing a suitable amount of dry powder compound medicament for multiple dosing by multi-dose dry powder inhalator 10. Storage chamber 18 includes an aperture 18A at the bottom thereof and an isolation plate 18B and biasing spring 18C which serves to isolate and stage the bulk powder compound from the ambient air.

Finally, a predetermined charge of dry powder medicament is delivered from storage chamber 18 to compound swirl chamber 16C of secondary air passageway 16 by metering plate 20A of dose introduction mechanism 20 (see particularly FIG. 4). Metering plate 20A of dose introduction mechanism 20 is slidably mounted within housing 12 of inhalator apparatus 10 so as to be normally retained in a first inoperative position wherein dry powder medicament-receiving aperture 20A' is located beneath and in registration with bottom aperture 18A of storage chamber 18. Metering plate 20A is further adapted to be slidably urged inwardly by depressing actuator button 20B to a second position wherein aperture 20A' is positioned within compound swirl chamber 16C of secondary air passageway 16 so as to discharge the metered dose of dry powder medicament into the air flow therein. Metering plate 20A will be normally urged into the first inoperative position by spring 20C which is seated at one end within actuator button 20B and at the other end against housing 12 of inhalator apparatus 10.

In use, as a patient commences inhalation, air flow is induced at inlet end 14A of primary air passageway 14 from the ambient air. The air pressure is reduced as the air flows through venturi 14C of primary air passageway 14, and subsequently the air pressure is increased as a result of the divergence of outward end 14B of primary passageway 14. However, the air velocity is somewhat lower at outward end 14B than at inlet end 14A as a result of secondary air being introduced at venturi throat 14C from compound swirl chamber 16C which is at atmospheric pressure due to fluid communication with the ambient air by means of air introduction portion 16A of secondary air passageway 16.

As the inhalation process intensifies, a magnitude of air pressure differential develops between compound swirl chamber 16C and venturi throat 14C. When the correct envelope of the air flow profile is entered, the previously referenced pressure differential magnitude is sufficient to swirl the dry powder compound out of swirl chamber 16C and into a locally turbulent air flow region at venturi throat 14C.

It will thus be seen that there has been described above a novel multi-dose dry powder inhalator which is designed to introduce dry powder medicament at an optimized arcuate pathway into the mouth and pharynx of the user.

It will be understood that various details of the invention may be changed without departing from the scope of the invention. Furthermore, the foregoing description is for the purpose of illustration only, and not for the purpose of limitation—the invention being defined by the claims.

What is claimed is:

1. A portable apparatus for the inhalation of a predetermined amount of a dry powder compound as an aerosol effluent, comprising:
   an elongate housing defining a primary air passageway therethrough comprising a generally inclined air inlet portion having a first end and a second end, said first end of said inclined portion adapted to introduce air flow into said elongate housing at an angle between about 5°-45° below a horizontal baseline and an air exit portion at said second end of said inclined portion for insertion into the mouth, said primary air passageway further comprising a venturi position substantially in the medial portion thereof between said air inlet portion and said air exit portion;
   a storage chamber formed in said housing for storing said compound to be inhaled;
   a secondary air passageway in said housing comprising an air introduction portion having a first end and a second end, said first end of said introduction portion adjacent said air inlet portion of said primary air passageway and said second end of said introduction portion fluidly communicating with said venturi portion of said primary air passageway, said secondary air passageway further comprising an enlarged compound swirl chamber between said air introduction portion and said other end thereof; and
   dose introduction means provided within said housing for transporting a predetermined portion of said compound from said storage chamber to said compound swirl chamber of said secondary air passageway;
   whereby during inhalation the pressure differential between said venturi portion of said primary air passageway and said swirl chamber of said secondary air passageway serves to swirl the compound out of said swirl chamber and into said primary air passageway, and whereby the air flow pathway through said apparatus serves to introduce the compound along an optimized arcuate trajectory to the pharynx and larynx.

2. A portable apparatus according to claim 1 wherein said air inlet portion comprises means for introducing air flow into said elongate housing at an angle of about 15° below a horizontal baseline.

3. A portable apparatus according to claim 1 wherein said elongate housing has an inlet end and an outlet end, said air inlet portion is positioned vertically lower at said inlet end of said elongate housing with respect to said horizontal baseline than said air exit portion at said outlet end of said elongate housing.

4. A portable apparatus according to claim 1 wherein said storage chamber is provided with a spring biased plate element to urge a compound therein toward said dose introduction means.

5. A portable apparatus according to claim 1 wherein said air introduction portion of said secondary air passageway is in fluid communication with and extends generally above and lengthwise relative to said air inlet portion of said primary air passageway in said elongate housing.

6. A portable apparatus according to claim 5 wherein said swirl chamber of said secondary air passageway is positioned generally above said venturi portion of said primary air passageway and defines a generally cylindrically-shaped chamber.

7. A portable apparatus according to claim 1 wherein said dose introduction means comprises a slidable metering plate with a compound-receiving aperture therein adapted to be slidably moved from a normally inoperative position with said aperture beneath said storage chamber to an operative position with said aperture introduced into said swirl chamber of said secondary air passageway.

8. A portable apparatus according to claim 7 wherein said dose introduction means further comprises an inwardly deflectable actuator button and said slidable metering plate is actuated by said inwardly deflectable actuator button mounted in said elongate housing of said inhalator apparatus.

9. A portable apparatus for the inhalation of a predetermined amount of a dry powder compound as an aerosol effluent, comprising:
   an elongate housing defining a primary air passageway therethrough comprising a generally inclined air inlet portion having a first end and a second end, said first end of said inclined portion adapted to introduce air flow into said elongate housing at an angle of about 15° below a horizontal baseline and an air exit portion at the said second end of said inclined portion for insertion into the mouth, said primary air passageway further comprising a venturi position substantially in the medial portion thereof between said air inlet portion and said air exit portion;

a storage chamber formed in said housing for storing said compound to be inhaled;

a secondary air passageway in said housing comprising an air introduction portion having a first end and a second end, said first end of said introduction portion fluidly communicating with and extending generally above and lengthwise relative to said air inlet portion of said primary air passageway, and said second end of said introduction portion fluidly communicating with said venturi portion of said primary air passageway, said secondary air passageway further comprising an enlarged compound swirl chamber between said air introduction portion and said other end thereof; and dose introduction means provided within said housing for transporting a predetermined portion of said compound from said storage chamber to said compound swirl chamber of said secondary air passageway;

whereby during inhalation the pressure differential between said venturi portion of said primary air passageway and said swirl chamber of said secondary air passageway serves to swirl the compound out of said swirl chamber and into said primary air passageway, and whereby the air flow pathway through said apparatus serves to introduce the compound along an optimized arcuate trajectory to the pharynx and larynx.

10. A portable apparatus according to claim 9 wherein said elongate housing has an inlet end and an outlet end, said air inlet portion is positioned vertically lower at said inlet end of said elongate housing with respect to said horizontal baseline than said air exit portion at said outlet end of said elongate housing.

11. A portable apparatus according to claim 9 wherein said storage chamber is provided with a spring biased plate element to urge a compound therein toward said dose introduction means.

12. A portable apparatus according to claim 11 wherein said swirl chamber of said secondary air passageway is positioned generally above said venturi portion of said primary air passageway and defines a generally cylindrically-shaped chamber.

13. A portable apparatus according to claim 9 wherein said dose introduction means comprises a slidable metering plate with a compound-receiving aperture therein adapted to be slidably moved from a normally inoperative position with said aperture beneath said storage chamber to an operative position with said aperture introduced into said swirl chamber of said secondary air passageway.

14. A portable apparatus according to claim 13 wherein said dose introduction means further comprises an inwardly deflectable actuator button and said slidable metering plate is actuated by said inwardly deflectable actuator button mounted in said elongate housing of said inhalator apparatus.

* * * * *